United States Patent
Lee et al.

(10) Patent No.: US 7,238,200 B2
(45) Date of Patent: Jul. 3, 2007

(54) APPARATUS AND METHODS FOR MAKING LEAFLETS AND VALVE PROSTHESES INCLUDING SUCH LEAFLETS

(75) Inventors: Shouyan Lee, Rancho Santa Margarita, CA (US); Ernest Lane, Huntington Beach, CA (US)

(73) Assignee: Arbor Surgical Technologies, Inc., Irvine, CA (US)

( * ) Notice: Subject to any disclaimer, the term of this patent is extended or adjusted under 35 U.S.C. 154(b) by 0 days.

(21) Appl. No.: 11/144,254

(22) Filed: Jun. 3, 2005

(65) Prior Publication Data

US 2006/0276888 A1   Dec. 7, 2006

(51) Int. Cl.
  *A61F 2/24*  (2006.01)
(52) U.S. Cl. ..................... 623/2.14; 623/901
(58) Field of Classification Search ...... 623/2.12–2.19, 623/901
See application file for complete search history.

(56) References Cited

U.S. PATENT DOCUMENTS

| | | | |
|---|---|---|---|
| 3,744,060 A | | 7/1973 | Bellhouse |
| 4,259,753 A | | 4/1981 | Liotta et al. |
| 4,451,936 A | | 6/1984 | Carpentier et al. |
| 4,501,030 A | * | 2/1985 | Lane ............ 623/2.18 |
| 4,666,442 A | | 5/1987 | Arru et al. |
| 4,687,483 A | * | 8/1987 | Fisher et al. ............ 623/2.14 |
| 4,692,164 A | * | 9/1987 | Dzemeshkevich et al. . 623/2.14 |
| 4,851,000 A | | 7/1989 | Gupta |
| 5,037,434 A | | 8/1991 | Lane |
| 5,147,391 A | | 9/1992 | Lane |
| 5,469,868 A | | 11/1995 | Reger |
| 5,549,665 A | | 8/1996 | Vesely et al. |
| 5,662,705 A | * | 9/1997 | Love et al. ............ 128/898 |
| 5,928,281 A | * | 7/1999 | Huynh et al. ............ 623/2.14 |
| 5,961,549 A | * | 10/1999 | Nguyen et al. ............ 623/2.12 |
| 5,984,959 A | | 11/1999 | Robertson et al. |
| 6,059,827 A | | 5/2000 | Fenton, Jr. |

(Continued)

FOREIGN PATENT DOCUMENTS

WO    WO 03063740 A1 *  8/2003

OTHER PUBLICATIONS

PCT International Search Report for PCT/US2006/021391 (WO2006/132948), Applicant: Arbor Surgical Technologies, Inc., Form PCT/ISA/210 (5 pgs) and Form PCT/ISA/237 (6 pgs), Sep. 22, 2006.

*Primary Examiner*—Corrine McDermott
*Assistant Examiner*—Thomas J. Sweet
(74) *Attorney, Agent, or Firm*—Vista IP Law Group LLP; William A. English

(57) ABSTRACT

A method for making a bioprosthetic heart valve includes providing a non-contact cutting apparatus and a layer of tissue. The non-contact cutting apparatus may include a laser cutting system or high pressure water jet system. A leaflet is cut from the layer of tissue using a predefined template, and a plurality of alignment holes in the leaflet are created in the leaflet, e.g., along a peripheral edge. A support structure is provided having a plurality of alignment holes corresponding to alignment holes in the leaflet. The leaflet is secured to the support structure by securing one or more sutures through corresponding alignment holes in the leaflet and the support structure to provide a leaflet subassembly. A bioprosthetic heart valve is made by securing a set of leaflet subassemblies to a frame.

28 Claims, 7 Drawing Sheets

U.S. PATENT DOCUMENTS

| | | |
|---|---|---|
| 6,168,614 B1 | 1/2001 | Andersen et al. |
| 6,254,636 B1 | 7/2001 | Peredo |
| 6,334,873 B1 * | 1/2002 | Lane et al. ................ 623/2.14 |
| 6,371,983 B1 | 4/2002 | Lane |
| 6,454,799 B1 | 9/2002 | Schreck |
| 6,461,382 B1 | 10/2002 | Cao |
| 6,468,305 B1 | 10/2002 | Otte |
| 6,709,457 B1 | 3/2004 | Otte et al. |
| 6,716,244 B2 | 4/2004 | Klaco |
| 6,733,525 B2 * | 5/2004 | Yang et al. ................ 623/2.18 |
| 6,797,000 B2 * | 9/2004 | Simpson et al. ........... 623/2.15 |
| 6,872,226 B2 | 3/2005 | Cali et al. |
| 2001/0039450 A1 * | 11/2001 | Pavcnik et al. ............ 623/1.24 |
| 2002/0116053 A1 * | 8/2002 | Simpson et al. ........... 623/1.26 |
| 2003/0023302 A1 | 1/2003 | Moe et al. |
| 2003/0139805 A1 * | 7/2003 | Holmberg et al. ......... 623/1.31 |
| 2003/0167089 A1 | 9/2003 | Lane |
| 2004/0015232 A1 | 1/2004 | Shu et al. |
| 2004/0030381 A1 | 2/2004 | Shu |

* cited by examiner

APPARATUS AND METHODS FOR MAKING LEAFLETS AND VALVE PROSTHESES INCLUDING SUCH LEAFLETS

FIELD OF THE INVENTION

The present invention relates generally to apparatus and methods for making bioprosthetic valve assemblies, and more particularly, to apparatus and methods for forming valve leaflets including alignment holes, e.g., from biological tissue, and for assembling such leaflets into laminate assemblies and/or prosthetic heart valves.

BACKGROUND

Bioprosthetic heart valves can replace defective native or previous prosthetic valves in patients. Bioprosthetic heart valves generally include a plurality of leaflets attached or otherwise coupled to a frame, stent, or other support structure. The leaflets may be formed from a synthetic material or biological tissue, such as bovine pericardium.

Sutures may be used to secure the leaflets to the support structure of the valve. Typically, a person, such as physician or even a specially trained seamstress, uses a needle and suture thread to pass one or more sutures through the leaflet and the support structure. This process is generally a manual operation and, consequently, may introduce a degree of variation between different sutures placed on a single valve. For example, the placement or even tightness of the individual sutures on a prosthetic valve may vary to some extent even with the most skilled artisan. The variation in which the sutures are placed in the valve may adversely impact the hemodynamic performance of the leaflets after they are secured to the support structure. For example, the particular location of a suture may impact the stress and/or strain characteristics of the leaflet.

In addition, in a multiple leaflet prosthetic valve, one or more leaflets may have different performance characteristics from the remaining leaflets because one or more sutures are inserted slightly off from their desired locations. Variability is thus introduced within a single valve (e.g. intra-valve variability), which may adversely impact the valve's hemodynamic performance. Similarly, even if there is no variability between individual leaflets on a single valve, variability may be introduced between different valves (e.g., inter-valve variability). This latter problem may arise, for example, because a number of different persons are employed to affix the individual leaflets to support structures or otherwise assemble the valves.

U.S. Pat. No. 5,662,705 discloses a method of manufacturing and testing a tissue heart valve during open heart surgery. A piece of autologous tissue from the body of the patient is cut with a plurality of holes being formed in the tissue by a cutting die. The tissue is situated between first and second stents so that the holes are registered with corresponding tissue alignment members in one of the stents, and the stents are positioned together to securely clamp the tissue therebetween.

In some prosthetic heart valve designs, the suture holes may be located close to the edge of the leaflets. When such leaflets are formed from bovine pericardium or other biological tissue, a die cutter may have difficulty punching or otherwise forming holes near or adjacent to the edge of the leaflets.

Thus, apparatus and methods for making leaflets and/or prosthetic valves that reduce intra-valve and/or inter-valve variability may be useful.

SUMMARY OF THE INVENTION

The present invention is directed generally to prosthetic valve assemblies and to apparatus and methods for making them, and, more particularly, to apparatus and methods for forming leaflets, e.g., from biological tissue, and/or for securing leaflets to a frame or other support structure using alignment holes formed in the leaflets, e.g., to make prosthetic valve assemblies. The alignment holes may accurately and/or precisely secure the leaflets to the support structure using standard suturing techniques. The present invention is also directed to leaflet laminate components, valve members, and other structures, and to apparatus and methods for assembling them.

In accordance with a first embodiment, a method is provided for forming a bioprosthetic heart valve from a layer of tissue using a cutting apparatus, e.g., a non-contact cutting apparatus, such as a laser cutting system or high-pressure water jet system. Alternatively, a die-cutter or other mechanical cutter may be used.

One or more leaflets may be cut from the layer of tissue, e.g., using a predefined template, which may include forming a plurality of alignment holes in the leaflet(s). A support structure may be provided having a plurality of alignment holes corresponding to alignment holes in each leaflet. The leaflet may be secured to the support structure, e.g., by securing one or more sutures through each set of alignment holes in the leaflet and the support structure.

In one embodiment, the leaflet may include a generally flat edge defining opposing ends, and a crescent-shaped base extending from the edge to define an apex. The leaflet may include at least three alignment holes, e.g., one hole located at or adjacent the apex, and one alignment hole located at or near each opposing end. Optionally, the leaflet may include one or more additional alignment holes, e.g., along one or more edges between the three alignment holes just described. For example, alignment holes may be provided in the leaflet that are arranged symmetrically about an axis intersecting the alignment hole located at the apex of the leaflet.

In accordance with another embodiment, a bioprosthetic heart valve includes a frame and one or more leaflet support structures carrying valve leaflets. The valve may have multiple leaflet support structures, e.g., three, that may be disposed substantially symmetrically around the frame. Each leaflet and support structure may include a plurality of alignment holes therein. The leaflets may be secured to the support structures, e.g., by one or more sutures extending through the alignment holes in the leaflets and support structures.

In one embodiment, each leaflet support structure may include a crescent-shaped strut and/or a laminate structure. For example, the support structure may include a curved strut having an alignment hole located at its apex and an alignment hole at each end of the strut. The holes in the leaflet may be arranged symmetrically about the leaflet in a similar configuration to facilitate securing the leaflet to the support structure.

Other aspects and features of the present invention will become apparent from consideration of the following description taken in conjunction with the accompanying drawings.

DETAILED DESCRIPTION OF THE PREFERRED EMBODIMENTS

Figure 1:
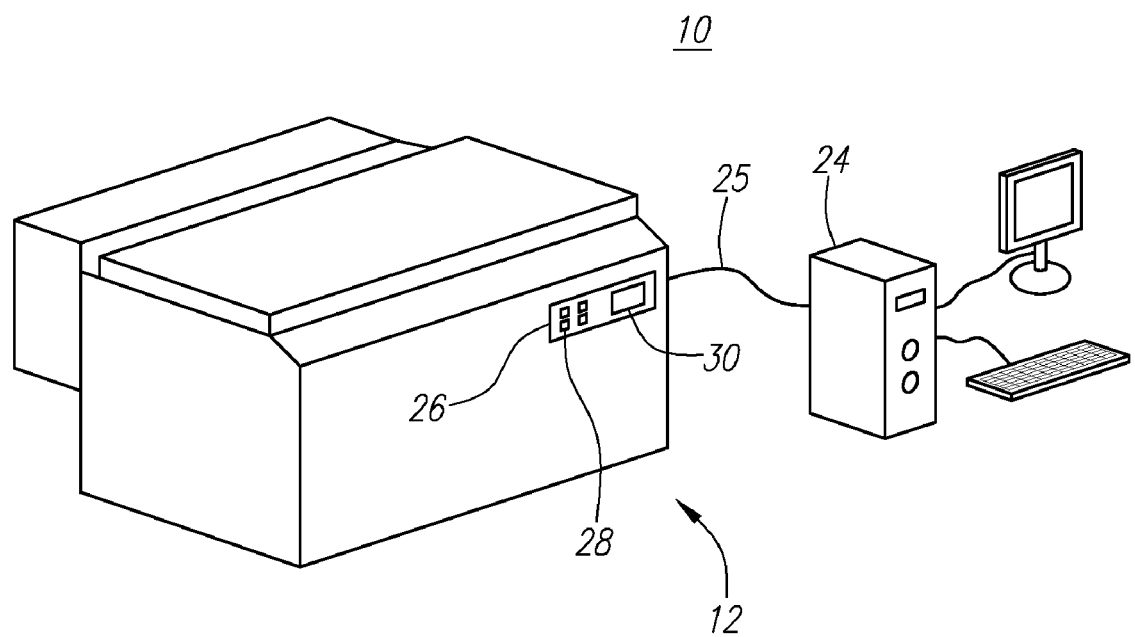
FIG. 1 illustrates a non-contact (e.g. laser-based) cutting apparatus for forming bioprosthetic leaflets.
Figure 2:
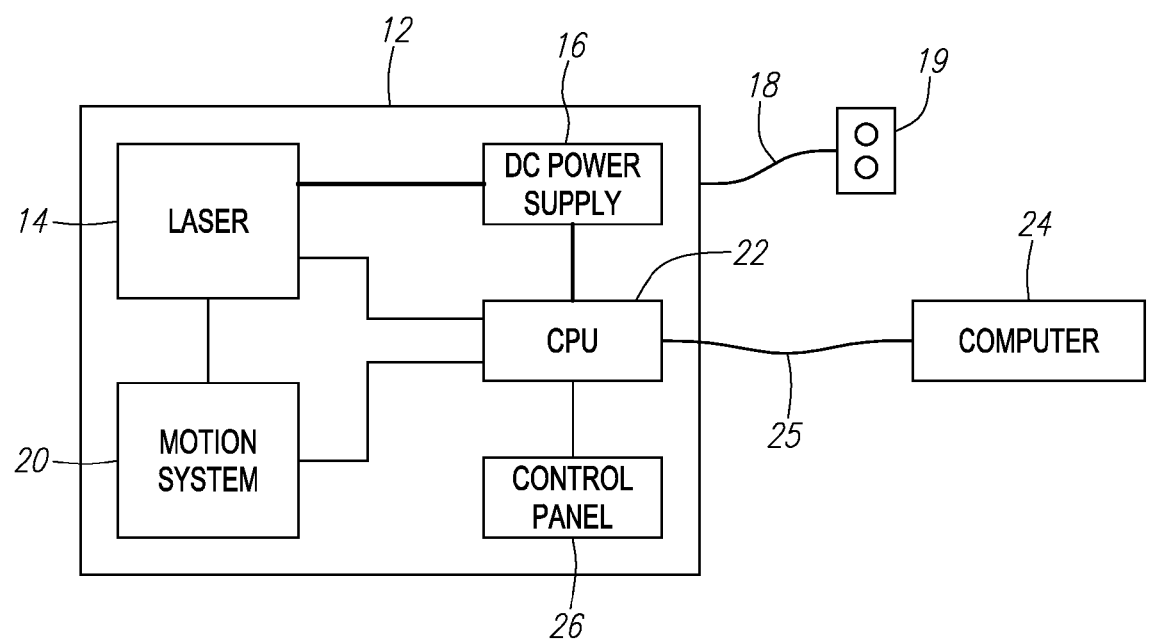
FIG. 2 illustrates exemplary components of the laser-based system of FIG. 1.

Turning to the drawings, FIGS. 1 and 2 show an exemplary embodiment of a cutting apparatus 10, i.e., a computer controlled laser system 12. As best seen in FIG. 2, the laser system 12 includes a laser source 14 powered by a DC power supply 16, which in turn, is connected to an AC power cord 18. The AC power cord 18 may be plugged into a standard 110/220 VAC outlet 19 or other power source (not shown). The laser source 14 may be a pulsed laser source, such as a pulsed $CO_2$ laser operating at a wavelength of 10.6μ. The DC power supply 16 may power the laser source 14, as well as the other electronic components of the laser system 12.

The laser system 12 includes a motion system 20 that enables the laser beam 38 (not shown, see, e.g., FIG. 3) emitted from the laser source 14 to traverse or follow a pre-determined path to cut a target material 34, such as biological tissue. In an exemplary embodiment, the motion system 20 may move in both X and Y directions (see, e.g., FIG. 3), and may coordinate movement of the mirror(s) and focusing lens (not shown) as the laser beam 38 tracks the pre-determined path.

Returning to FIGS. 1 and 2, the laser system 12 may include a central processing unit (CPU) 22 that controls the firing of the laser source 14 and the movement of the motion system 20. The CPU 22 may be powered by the DC power supply 16 and may include standard computer memory SIMMS where incoming files from computer 24 are stored when the laser system 12 is activated. The CPU 22 may be coupled to a control panel 26, which is typically located on the laser system 12 (best seen in FIG. 1). The control panel 26 may include a plurality of buttons 28 and/or a display 30, such as an LCD, CRT, and the like. The control panel 26 may be used to position the motion system 20, move within the menu system on the display 30, as well as run the laser system 12.

Figure 3:
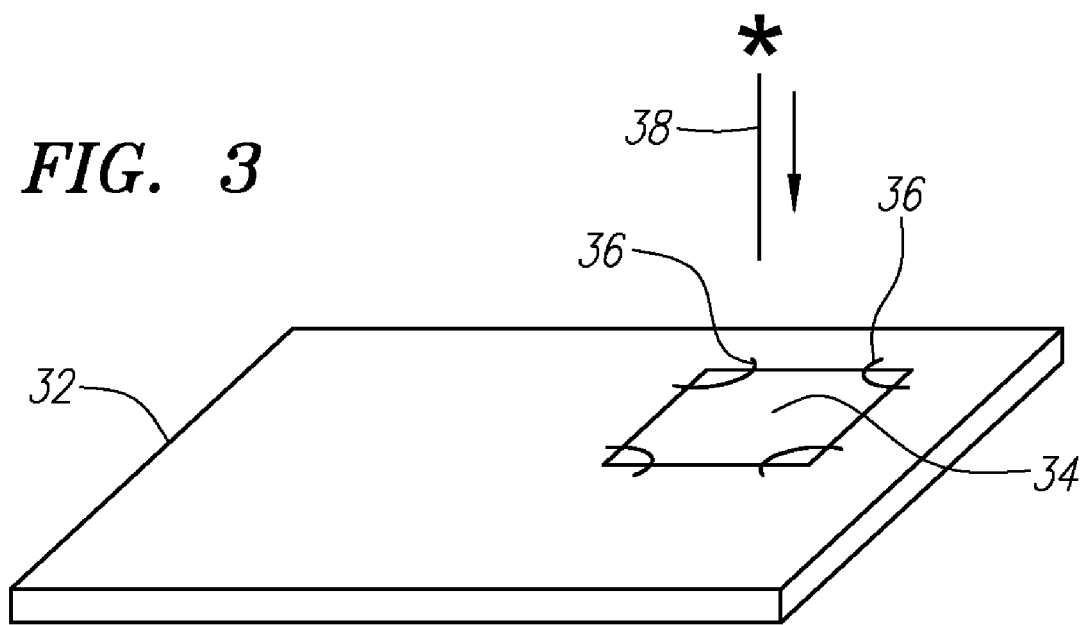
FIG. 3 illustrates a target material located on a table of a laser system, such as that shown in FIG. 2.

The computer 24 may be used to prepare or store one or more templates or targets paths used to cut the target material 34 (as shown in FIG. 3). In this manner, the computer 24 may allow one or more templates created using graphic software programs to interface with the laser system 12. Commercial graphic software programs such as CORELDRAW, MACROMEDIA FREEHAND, or ADOBE PHOTOSHOP, or CAD software such as AUTOSKETCH, DESIGNCAD, or AUTOCAD may be used to create the template or target path for the laser system 12. A data cable 25 and the like may connect the computer 24 to the CPU 22 such that data may be transferred to and from these components.

One exemplary laser system 12 that may be used is the M-300 Laser Platform manufactured by Universal Laser Systems, Inc. of Scottsdale, Ariz. This laser system 12 may allow a number of settings or parameters for the laser system 12 to be adjusted, including, for example, the power of the laser source 14 (Watts), the speed at which the laser beam moves over the target material 34 (inches/second), and/or the number of pulses delivered over a specific length of target material 34 (pulses per inch (PPI)). In one embodiment, for example, when the target tissue 34 is bovine pericardium, the power may be set to about thirty percent (30%) of the base power (e.g., thirty Watts (30 W)), the speed may be set to about 5.3% of the base speed (e.g., fifty five inches per second (55 in/s)), and the PPI may be set at about one thousand (1000). This setting may yield an energy per pulse of approximately 0.0030874 (Joules/pulse). This setting may be suitable to cut the leaflets 40 as well as form the alignment holes 42 in the pericardium tissue, e.g., to form leaflets 40 having a thickness up to approximately 0.027 inch. Generally, the leaflets 40 may be formed using tissue having a thickness between about 0.015-0.024 inch.

With reference to FIG. 3, the laser system 12 may include a table 32 that holds the material 34 that is to be cut and/or drilled with the laser system 12. The table 32 generally includes a planar surface on which the material 34 is placed. Because the material 34 is typically wet or moist, the material 34 may simply be placed on top of the table 32, i.e., the surface tension of the moisture may substantially secure the material 34 to the table 32. Alternatively, as is shown in FIG. 3, the table 32 may include one or more retaining members 36, e.g., pins and the like, to hold the target material 34 in place during the laser operation. Alternatively, the table 32 may include a number of holes or slits (not shown) to create a vacuum chuck for holding the target material 34 substantially securely to the surface of the table 32. The table 32 is generally oriented orthogonal to the direction of the laser beam 38 as is shown in FIG. 3.

Figure 4:
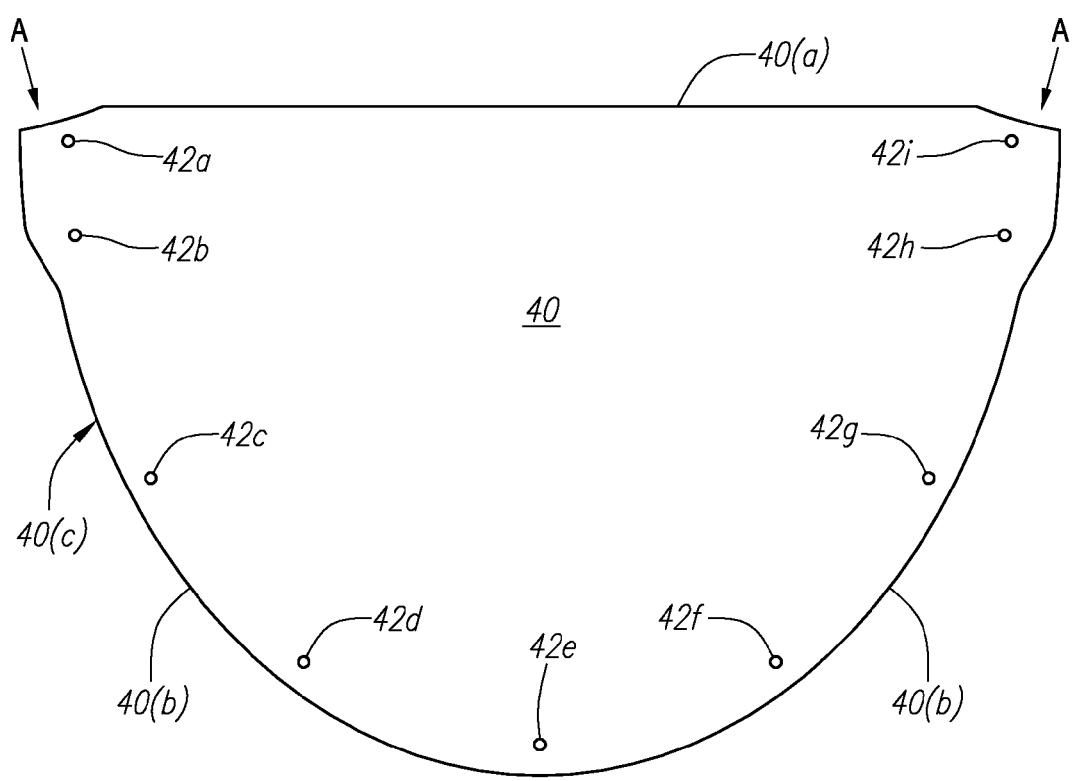
FIG. 4 is an enlarged plan view of a bioprosthetic leaflet having a plurality of pre-formed alignment holes therein.

With reference now to FIG. 4, a leaflet 40 is shown that may be cut and drilled using the systems and methods described herein. The leaflet 40 may be formed from biological tissue, such as bovine pericardium, and may include a generally flat portion 40a and an outwardly projecting scalloped or curved portion 40b defined by a peripheral edge 40c. As shown, the leaflet 40 includes a plurality of holes 42a-42i drilled or otherwise formed adjacent to the peripheral edge 40c of the scalloped portion 40b of the leaflet 40. In an exemplary embodiment, the holes 42a-42i may be provide in from the peripheral edge 40c of the leaflet by about 0.025 inch. The plurality of holes 42a-42i may be drilled or otherwise formed before cutting the peripheral edge 40c of the leaflet 40. Alternatively, the peripheral edge 40c of the leaflet 40 may be formed before forming the holes 42a-42i. In yet another alternative, the holes 42a-42i may be formed generally at the same time as the peripheral edge 40c of the leaflet 40 is cut.

In one embodiment, a portion of the leaflet 40 adjacent to the flat portion 40a may be flared or otherwise may project outwardly, as shown by arrows A in FIG. 4. This configuration may enable the flared portion of the leaflet 40 to partially or completely wrap around a support structure (not shown), as explained further below.

At least some of the holes 42a-42i in the leaflet 40 may be located to correspond with alignment holes in a frame or other support member, such as alignment holes 54 shown in struts 52 in FIGS. 5A and 5C, and described further below. In one embodiment, the holes 42a-42i may be symmetrically arranged in a bilateral manner about an axis, e.g., passing vertically through the apex of the curved portion 40b, e.g., substantially symmetrically about hole 42e. FIG. 4 illustrates a total of nine holes 42a-42i distributed along the peripheral edge 40c of the leaflet 40, although a higher or lower number may be provided, if desired. The diameter of the holes 42a-42i may range from about 0.006-0.012 inch, and in an exemplary embodiment, may be about 0.008 inch.

Figure 5A:
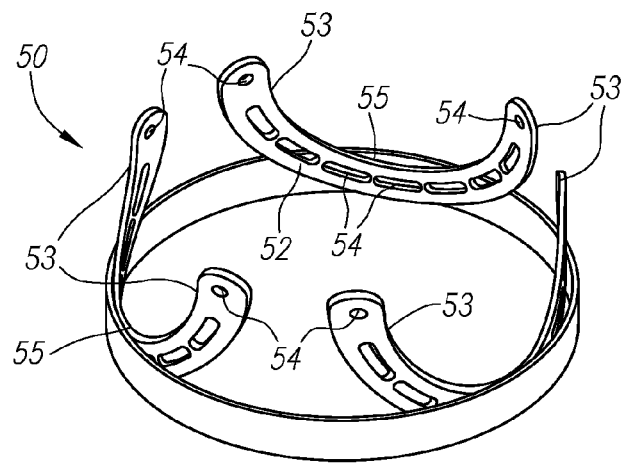
FIG. 5A is a perspective view of an exemplary embodiment of a valve frame that may be included in a valve assembly.
Figure 5B:
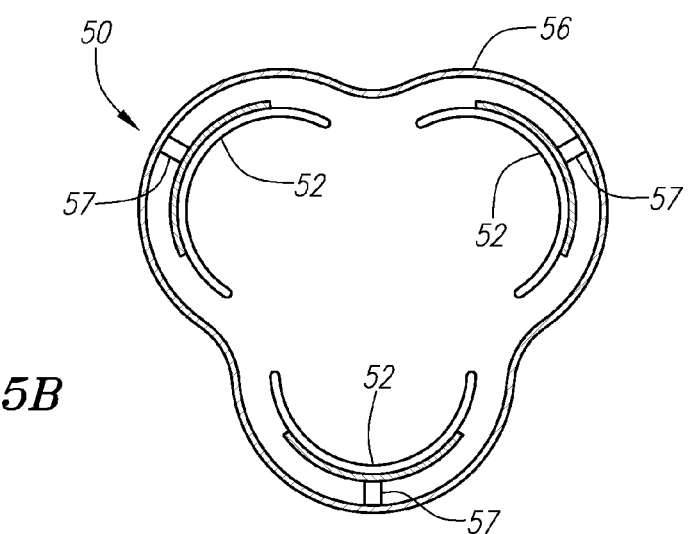
FIG. 5B is a top view of the valve frame and support structures shown in FIG. 5A.
Figure 5C:
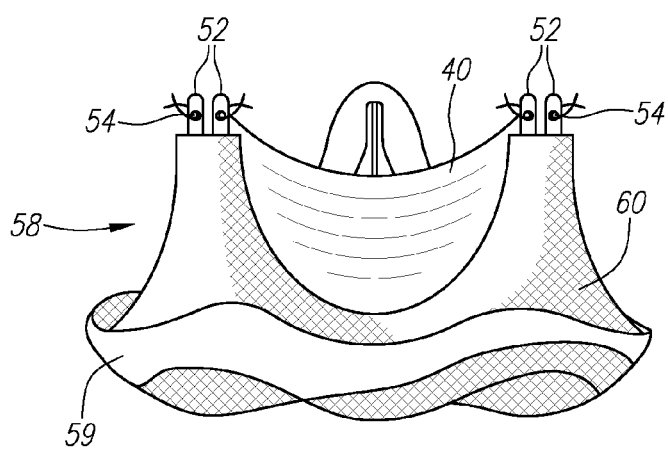
FIG. 5C is a side view of a one-piece valve including the frame and support structures of FIGS. 5A and 5B, a plurality of leaflets, and a fabric covering.

FIGS. 5A-5C show an exemplary embodiment of a prosthetic valve frame 50 that may carry a plurality of leaflets 40, e.g., to provide a bioprosthetic heart valve assembly 58. The valve frame 50 may include one or more struts or other leaflet support structures 52 having a plurality of alignment holes 54 therein. For example, the support structures 52 may be "U" or crescent-shaped struts having opposite ends 53 between a curved intermediate region 55. In one embodiment, each support structure 52 may be a laminate structure, e.g., including two or more struts disposed adjacent one another such that the ends 53 are more flexible than the intermediate region 55. Additional information regarding the lengths and/or construction of the components of such laminates may be found in U.S. Pat. No. 6,371,983, the entire disclosure of which is expressly incorporated by reference herein.

The alignment holes 54 may be drilled, laser cut, mechanically cut, or otherwise formed in the support structures 52, e.g., at locations corresponding to the holes 42 formed in the leaflet 40. For example, the alignment holes 54 may be created before or after cutting the support structures 52 from base material, e.g., using similar methods used to form the alignment holes 54. In the embodiment shown in FIGS. 5A-5C, the valve frame 50 includes three leaflet support structures 52, each having three alignment holes 54. As best seen in FIG. 5A, one alignment hole 54 may be located at the base of the intermediate region 55 of the support structure 52 while two additional alignment holes 52 may be located at the ends 53 of the support structure 52. With reference to FIGS. 4 and 5A, the alignment holes 54 at the ends 53 of the support structure 52 may align with alignment holes 42a and 42i of the leaflet 40. The alignment hole 54 located at the base of the support structure 52 may align with the alignment hole 42e located at the apex of the leaflet 40.

In one embodiment, before securing the leaflet 40 to the support structure 52, the support structure 52 may be covered with fabric or other sheet material, such as Dacron fabric, and the like. Such a covering may enhance fatigue strength of the assembly valve assembly 58, may facilitate fastening and/or assembly of the valve assembly 58, and/or may allow tissue ingrowth into or around the valve assembly 58 after implantation.

FIGS. 5A-5C illustrate a valve 58 that includes three such support structures 52, each carrying a leaflet 40, thereby providing leaflet subassemblies or laminates. The leaflet subassemblies may be secured to an outer frame 56, e.g., using a spacer 57. The spacer 57 may permit the support structures 52 and the attached leaflets 40 to float at least partially relative to the outer frame 56. For example, a spacer 57 may be attached to the base or intermediate regions 55 of each support structure 52, thereby allowing the ends 53 of the support structures 52 to bend or otherwise deflect, e.g., inwardly, to accommodate movement of the leaflet 40. The spacers 57 may be secured to the support structures 52 and/or to the frame 56 using detents or other mechanical connectors, adhesives, welding, and the like. In an exemplary embodiment, each spacer 57 may include a plurality of tabs or other detents (not shown), and the support structure 52 and/or frame 56 may include holes or pockets (also not shown) into which the detents may be received.

As shown in FIG. 5C, the valve 58 includes a sewing ring or suture cuff 59, which may extend radially outwardly from the frame 56. The sewing cuff 59 may be made of a matrix or fabric that permits tissue ingrowth. As shown in FIG. 5C, the valve frame 50 may also be covered with fabric or other flexible material, e.g., fabric covering 60. The fabric covering 60 may act as a matrix for cell ingrowth, and/or may be easily penetrated with a needle and/or a fastener, e.g., used to attach the cuff 59 to an annulus within which the heart valve 58 is implanted. Exemplary fabric material may include polyester (e.g., DACRON® from E.I. du Pont de Nemours and Company, Wilmington, Del.), polypropylene, PTFE, ePTFE, nylon, extruded collagen, silicone, and/or combinations thereof.

In one embodiment, the sewing cuff 59 may be formed from the same section(s) of fabric covering the frame 56, e.g., which may be folded or otherwise gathered to adopt a radial or other desired configuration. Alternatively, the sewing cuff 59 may be a separate component attached or otherwise secured around the frame 56. Optionally, the sewing cuff 59 may include a core, which may support and/or bias the sewing cuff 59 to extend radially outwardly.

Figure 6:
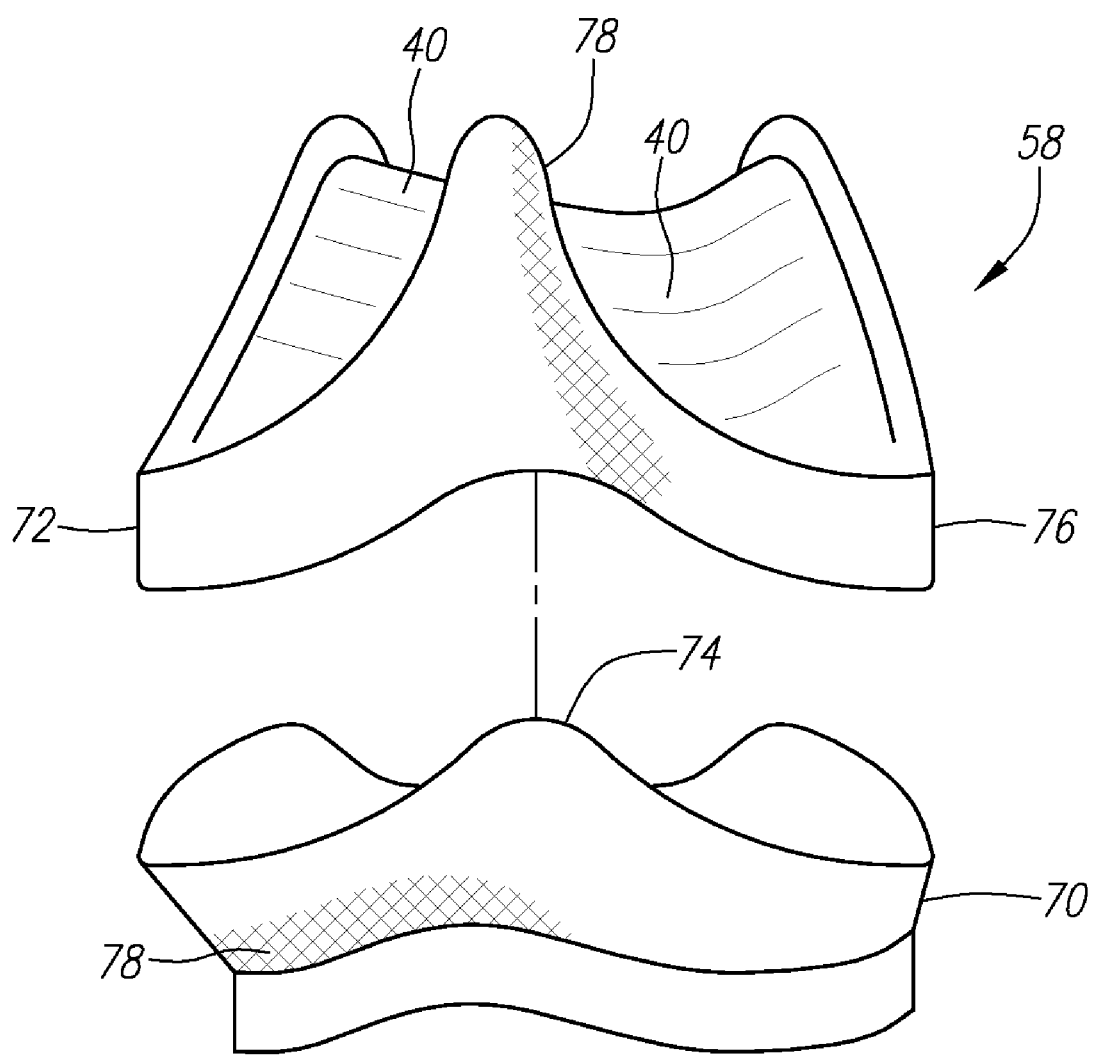
FIG. 6 is a perspective view of another embodiment of a two-piece valve including a valve member and a gasket member.

In an alternative embodiment, shown in FIG. 6, the valve 58' may include two parts, e.g., generally including a base or "gasket member" 70 and a valve member or "crown" 72. The gasket member 70 is a generally annular shaped body that may have a substantially circular and/or non-circular shape. For example, the gasket member 70 may include an annular portion 73, which may have a substantially circular shape, and a sewing cuff portion 74, which may extend radially outwardly and/or upwardly from the annular portion 73. In one embodiment, the sewing cuff portion 74 may have a tri-lobular or other multiple lobular shape, e.g., including three lobes separated by cusps or scallops. Optionally, the annular portion 73 may be radially expandable and/or compressible, e.g., to facilitate introduction into a tissue annulus and/or to dilate the tissue annulus (not shown). Additional information on a gasket member that may be provided may be found in co-pending application Ser. Nos. 11/069,081, filed Feb. 28, 2005 and 60/669,704, filed Apr. 8, 2005. The entire disclosures of these applications are expressly incorporated by reference herein.

The crown 72 generally includes an annular shaped body or frame 76 and one or more leaflet subassemblies, such as those described elsewhere herein. Thus, the crown 72 may be a prosthetic valve member, i.e., an annular frame 76 carrying a plurality of tissue leaflets 40 carried by support structures 52 (as shown, for example, in FIGS. 5A-5C). The frame 76 may have a non-circular, e.g., multiple lobular shape, e.g., complementary to a supra-annular space within which the valve 58' is to be implanted.

For example, in one embodiment, the frame 76 may have a tri-lobular shape, e.g., similar to the aortic root above an aortic valve site (not shown) and/or similar to the sewing cuff 74 of the gasket member 70. In addition, the frame 76 may have a sinusoidal or other serpentine lower edge, which may facilitate implantation at a tissue annulus and/or docking with the gasket member 70. U.S. patent application Ser. No. 11/069,081, incorporated above, discloses various embodiments of valve members that may be provided for the crown 72, as well as structures and methods for connecting the crown 72 to the gasket member 70. As seen in FIG. 6, the gasket member 70 and crown 72 may be covered with a fabric, or other flexible material, e.g., fabric covering 78, similar to the previous embodiments.

Figure 7A:
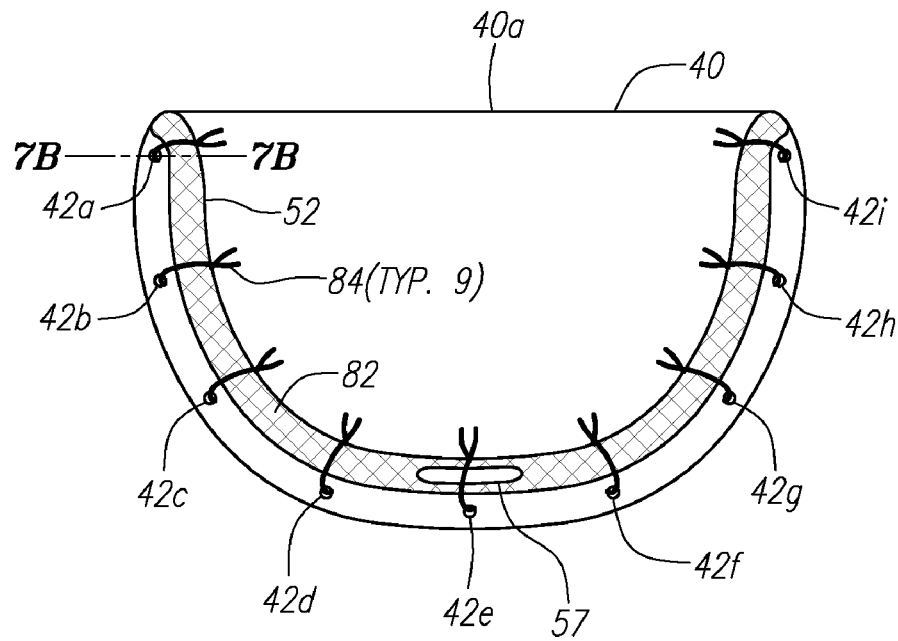
FIG. 7A illustrates a leaflet support structure sub-assembly.
Figure 7B:
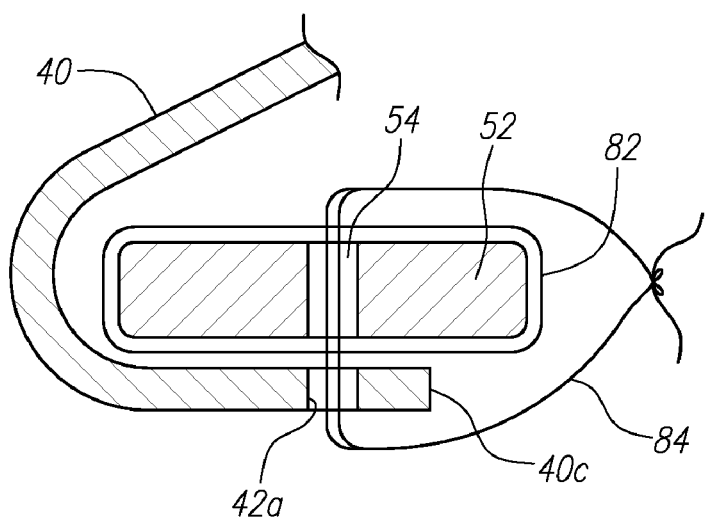
FIG. 7B is a detail of the leaflet support structure sub-assembly of FIG. 7A, taken along the line A-A.

In one or more of the embodiments described herein, e.g., the valve 58' shown in FIG. 6, may be constructed by first forming a set of leaflet sub-assemblies 80, such as those shown in FIGS. 7A and 7B. Typically, three such sub-assemblies 80 may be needed for a complete aortic valve 58, e.g., intended to replace a native or other prosthetic aortic valve (not shown). Each sub-assembly 80 may include a support structure 52, for example, a crescent-shaped strut including a plurality of laminate members (not shown). For example, each laminate member may be laser cut or otherwise formed from Nitinol, Elgiloy or other flexible, elastic, and/or superelastic material.

If the support structure 52 includes multiple laminate members, the laminate members may be aligned within one another into the crescent shape (e.g., aligned symmetrically about their bases), the laminate members may be covered with cloth or other fabric covering, as described elsewhere herein. The laminate members may remain separate from one another but constrained within the fabric covering. Alternatively, the laminate members may be connected to one another at one or more locations, e.g., at their bases.

The fabric covering may be secured around the support structure 52, e.g., using sutures, and the like (not shown). Each sub-assembly 80 also includes a spacer 57 secured at the base or intermediate region 55 of the support structure 52, as described above. The spacer 57 may be connected to the outer most laminate member of a laminate structure, or may be coupled to each of the laminate members. The spacer 57 may be secured to the support structure 52 before or after being covered with fabric.

The leaflet 40 is then secured to the support structure 52, e.g., using one or more sutures or other filaments. For example, the peripheral edge 40c of the leaflet 40 may be folded or otherwise directed at least partially around the support structure 52, e.g., around the outer edge of the support structure 52, until the alignment holes 42a-42i in the leaflet 40 (as seen in FIG. 4) are aligned with corresponding alignment holes 54 in the support structure 52. Alternatively, the leaflet 40 may be lain flat over the support structure 52 such that the alignment holes 42, 54 are aligned, e.g., such that the peripheral edge 40c of the leaflet 40 follows generally along an outer edge of the support structure 52. As described above, in one embodiment, the support structure 52 may include three alignment holes 54, which may be aligned with three of the alignments holes 42 on the leaflet 40, e.g., alignment holes 42a, 42e, 42i (best seen in FIGS. 4 and 5A).

A needle or other instrument (not shown) having a suture 84 or other filament attached thereto may be directed through each leaflet alignment hole 42 (e.g., 42a, 42e, 42i) and the corresponding alignment hole 54 in the support structure 52. The individual sutures 84 may be cut and/or tied off, e.g., as is shown in FIGS. 7A and 7B. Optionally, the leaflet 40 may be further secured to the support structure 52 by passing the needle (carrying suture 84) through the remaining leaflet holes 42b, 42c, 42d, 42f, 42g, 42h and into the fabric 82 surrounding the support structure 52. With respect to these sutures 84, the leaflet 40 may be secured to the fabric 82 and not the underlying support structure 52. Alternatively, the remaining sutures 84 may also pass through leaflet alignment holes 42 and corresponding alignment holes 54 in the support structure 52, as described with respect the three sutures 84 located at the apex and ends 53 of the support structures 52.

After the leaflet-support structure sub-assemblies 80 have been made, the sub-assemblies 80 may be immersed in a bioburden reduction process (BRP) solution and/or otherwise treated or stored. For example, the BRP solution may be a glutaraldehyde and polysorbate-80 solution (i.e., TWEEN-80) or an aldehyde-polysorbate-80 solution. Exemplary solutions and methods for using them are disclosed in U.S. Pat. No. 4,885,005 (Nashef et al.) or in co-pending application Ser. No. 11/032,923, filed Jan. 11, 2005. The entire disclosures of these references are expressly incorporated by reference herein.

For example, sub-assemblies 80 may be submerged and heated in a BRP solution for a period of time between about four and twenty-four (4-24) hours at a temperature of around thirty-seven degrees Celsius (37° C.), e.g., at a ratio of about one hundred milliliters per valve (100 mL/valve) equivalent.

After the sub-assemblies 80 have undergone bioburden reduction, the sub-assemblies 80 may be assembled into a valve 58 (i.e., prosthetic heart valve). In one embodiment, this process may include assembling the leaflet sub-assemblies to a frame 56 using spacers 57. The spacers 57 may offset the leaflet subassemblies away from one another about the circumference or periphery of the frame 56, e.g., approximately one hundred twenty degrees (120°) for a heart valve including three leaflets 40. Optionally, if desired, the spacers 57 may space the leaflets 40 inwardly and/or upwardly away from the frame 56 or other structures of the heart valve, e.g., to prevent the leaflets 40 from rubbing or otherwise contacting the frame 56 during use (i.e., opening and closing), which may otherwise wear or damage the leaflet 40 over time.

For example, tabs or other detents on the spacers 57 may be snapped or otherwise secured at predetermined locations around the periphery of the frame 56. In an exemplary embodiment, three sub-assemblies 80 may be secured to the frame 56, e.g., distributed substantially evenly about the perimeter of the frame 56, e.g., approximately one hundred twenty degrees (120°) apart. Typically, as shown in FIG. 5C, the frame 56 may be covered with a fabric 60 to promote tissue ingrowth. At least a portion of the fabric covering 60 may be opened or removed to facilitate accessing the holes or pockets to secure the spacers 57. In addition or alternatively, if the valve 58 includes a sewing cuff (e.g., similar to sewing cuff 59, shown in FIG. 5C), a portion of the fabric 60 may be used to form a sewing cuff 59.

After assembly, the valve 58 may be tested using any desired testing methods. Typically, these tests may include coaptation tests and forward and/or backward flow tests. Tests may be performed to ensure that the assembled valves 58 open with minimal effort, close with minimal leakage, and/or provide suitable hemo or hydro-dynamic performance, e.g., at a wide range of operating flow conditions. The assembled heart valves 58 may also be visually inspected. The assembled heart valves 58 that pass the tests may be transferred to a final container where they may be subjected to a terminal liquid sterilization (TLS) process and/or otherwise stored, e.g., before shipment to hospitals for implantation by surgeons.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for making a bioprosthetic heart valve, comprising:
   creating a leaflet from a sheet of target material;
   creating a plurality of alignment holes in the leaflet along at least one peripheral edge of the leaflet;
   providing a crescent-shaped support structure having a concave edge, a convex edge, and a plurality of alignment holes corresponding to at least some of the alignment holes in the leaflet; and
   directing one or more sutures through the corresponding alignment holes in the leaflet and the support structure to secure the leaflet to the support structure.

2. The method of claim 1, wherein the leaflet and alignment holes are created using a non-contact cutting apparatus.

3. The method of claim 2, wherein the non-contact cutting apparatus comprises at least one of a laser cutting system and a high-pressure water jet system.

4. The method of claim 2, wherein the alignment holes in the leaflet are located within about 0.025 inch of the at least one peripheral edge of the leaflet.

5. The method of claim 2, wherein the alignment holes in the leaflet have a diameter between about 0.006-0.012 inch.

6. The method of claim 2, wherein the target material comprises biological tissue.

7. The method of claim 6, wherein the biological tissue comprises pericardium.

8. The method of claim 6, wherein the biological tissue has a thickness between about 0.015-0.024 inch.

9. The method of claim 1, wherein the alignment holes in the leaflet are symmetrically arranged about an apex of the leaflet.

10. The method of claim 1, further comprising directing one or more additional sutures through alignment holes in the leaflet and a fabric covering on the support structure.

11. The method of claim 1, securing the support structure to a valve frame.

12. The method of claim 11, wherein the support structure is secured to the valve frame by a spacer.

13. A method for making a bioprosthetic heart valve, comprising:
   creating a first leaflet from a sheet of target material, the first leaflet comprising a crescent-shaped edge;
   creating a plurality of alignment holes in the first leaflet along the crescent-shaped edge;
   providing a first crescent-shaped support structure having a concave edge, a convex edge, and a plurality of alignment holes corresponding to at least some of the alignment holes in the first leaflet; and
   directing one or more sutures through the corresponding alignment holes in the first leaflet and the first support structure to secure the first leaflet to the first support structure.

14. The method of claim 13, further comprising attaching the first support structure to a frame.

15. The method of claim 14, wherein the first support structure comprises an intermediate region between free ends thereof, and wherein the first support structure is attached to the frame at the intermediate region, thereby allowing the free ends to bend or deflect.

16. The method of claim 14, further comprising:
   creating a second leaflet from a sheet of target material, the second leaflet comprising a crescent-shaped edge;
   creating a plurality of alignment holes in the second leaflet along the crescent-shaped edge;
   providing a second crescent-shaped support structure having a concave edge, a convex edge, and a plurality of alignment holes corresponding to at least some of the alignment holes in the second leaflet;
   directing one or more sutures through the corresponding alignment holes in the second leaflet and the second support structure to secure the second leaflet to the second support structure; and
   attaching the second support structure to the frame such that the second support structure is offset about a periphery of the frame from the first support structure.

17. The method of claim 13, wherein the leaflet and alignment holes are created using a non-contact cutting apparatus.

18. The method of claim 13, wherein the non-contact cutting apparatus comprises at least one of a laser cutting system and a high-pressure water jet system.

19. The method of claim 13, wherein the target material comprises biological tissue.

20. The method of claim 13, wherein creating a plurality of alignment holes comprises creating an alignment hole at the apex of the crescent-shaped edge.

21. The method of claim 20, wherein creating a plurality of alignment holes comprises creating an alignment hole at each opposing end of the crescent-shaped edge.

22. A method for making a bioprosthetic heart valve using a plurality of leaflets, each leaflet comprising a crescent-shaped edge, comprising:
   creating a plurality of alignment holes along the crescent-shaped edge of each leaflet;
   providing a plurality of crescent-shaped struts, each strut comprising a plurality of alignment holes arranged similar to the alignment holes in each leaflet;
   directing one or more sutures through the corresponding alignment holes in each leaflet and a respective strut to secure the leaflet to the respective strut; and
   attaching the struts to an annular frame at intermediate regions of the struts, thereby allowing free ends of the struts to bend or deflect independent of one another, the struts being offset from one another about a periphery of the frame.

23. The method of claim 22, wherein attaching the struts comprises connecting spacers between the respective struts and the frame.

24. The method of claim 22, wherein the plurality of alignment holes are laser-cut in each leaflet.

25. A method for making a bioprosthetic heart valve, comprising:
   creating a plurality of leaflets from biological tissue;
   creating a plurality of alignment holes in each of the leaflets along at least one peripheral edge of the respective leaflets;
   providing a plurality of crescent-shaped support structures, each of the support structures having a curved intermediate region between opposite ends, and a plurality of alignment holes corresponding to at least some of the alignment holes in the leaflets; and
   directing one or more sutures through the corresponding alignment holes in the leaflets and the support structures to secure the leaflets to respective support structures, thereby providing a set of separate leaflet sub-assemblies.

26. The method of claim 25, further comprising attaching the leaflet sub-assemblies to a frame such that ends of adjacent support structures are disposed adjacent one another.

27. The method of claim 26, wherein the ends of the support structures are free to bend or deflect independent of one another.

28. The method of claim 25, wherein each of the support structures comprises a concave edge and a convex edge.

* * * * *